United States Patent
Ichikawa et al.

(10) Patent No.: US 9,326,845 B2
(45) Date of Patent: May 3, 2016

(54) INTRAOCULAR IMPLANT, INTRAOCULAR IMPLANT SET AND INTRAOCULAR LENS

(71) Applicant: CHUKYO MEDICAL CO., INC., Nagoya-shi, Aichi (JP)

(72) Inventors: Kazuo Ichikawa, Nagoya (JP); Norihiko Yoshida, Nagoya (JP)

(73) Assignee: CHUKYO MEDICAL CO., INC., Nagoya-Shi, Aichi (JP)

( * ) Notice: Subject to any disclaimer, the term of this patent is extended or adjusted under 35 U.S.C. 154(b) by 0 days.

(21) Appl. No.: 14/261,001

(22) Filed: Apr. 24, 2014

(65) Prior Publication Data

US 2015/0305856 A1 Oct. 29, 2015

(51) Int. Cl.
*A61F 2/16* (2006.01)

(52) U.S. Cl.
CPC ..... *A61F 2/1648* (2013.01); *A61F 2002/16902* (2015.04); *A61F 2220/0033* (2013.01)

(58) Field of Classification Search
CPC ... A61F 2/1613; A61F 2/1648; A61F 2/1629; A61F 2/1694; A61F 2/1635
USPC ........................ 623/6.4–6.41, 6.43
See application file for complete search history.

(56) References Cited

U.S. PATENT DOCUMENTS

| | | | | |
|---|---|---|---|---|
| 2008/0167715 A1* | 7/2008 | Brady et al. | ............... | 623/6.32 |
| 2010/0121444 A1* | 5/2010 | Ben Nun | ..................... | 623/6.34 |
| 2011/0040378 A1* | 2/2011 | Werblin | ..................... | 623/6.34 |

FOREIGN PATENT DOCUMENTS

| | | |
|---|---|---|
| DE | 3503690 C1 | 11/1986 |
| EP | 1138282 A1 | 10/2001 |
| JP | 560232150 A | 11/1985 |
| JP | H04113310 A | 4/1992 |
| JP | H08103457 A | 4/1996 |
| JP | 2792588 B2 | 9/1998 |
| JP | 2006288770 A | 10/2006 |
| JP | 2007518447 A | 7/2007 |

* cited by examiner

*Primary Examiner* — David H Willse
*Assistant Examiner* — Tiffany Shipmon
(74) *Attorney, Agent, or Firm* — Bacon & Thomas, PLLC (57) ABSTRACT

Provided are an intraocular implant, an intraocular implant set, and an intraocular lens in which the intraocular lens is easily replaced compared to the related art.

A support structure is a portion which is used to dispose an intraocular lens (a lens) (in a rear section) inside an eye and is formed separately from the lens. When the lens is attached to the support structure, a configuration is formed which is the same as that of the existing intraocular lens including a lens serving as an eye lens extracted due to the cataract or the like and a portion supporting the lens into an eye. The support structure and the lens may be integrated with each other inside the eye. An embodiment in which only the lens is replaced while the support structure is fixed into the eye and which is not present in the related art can be realized.

9 Claims, 9 Drawing Sheets

A-A CROSS SECTION

A-A CROSS SECTION

FIG. 8

A-A CROSS SECTION

FIG. 9

A-A CROSS SECTION

B-B CROSS SECTION

B-B CROSS SECTION

INTRAOCULAR IMPLANT, INTRAOCULAR IMPLANT SET AND INTRAOCULAR LENS

BACKGROUND OF THE INVENTION

1. Field of the Invention

The present invention relates to an intraocular implant, an intraocular implant set, and an intraocular lens.

2. Description of the Related Art

As widely known, a surgery operation has been widely performed in which a cloudy white eye lens of a patient is extracted and an intraocular lens (an aphakic intraocular lens) is transplanted into an eye as the treatment for the eye's cataract. For example, Japanese Patent No. 2792588 proposes an intraocular lens which is transplanted into an eye from which an eye lens is extracted and is sutured to a ciliary body in the treatment of the cataract.

PRIOR ART DOCUMENT

Patent Document

Patent Document 1: Japanese Patent No. 2792588

SUMMARY OF THE INVENTION

There is a case where a patient may complain an improper lens power after the intraocular lens transplanting operation. In that case, the patient wears eyeglasses to solve this inconvenience, but the replacement of the intraocular lens may be another option. However, it is generally known that the intraocular lens replacing operation is more difficult than the first transplanting operation, and hence it is important to develop a technique of more easily replacing the intraocular lens.

Therefore, the invention is made in view of the above-described circumstances, and an object thereof is to provide an intraocular implant, an intraocular implant set, and an intraocular lens in which the intraocular lens is easily replaced compared to the related art.

Problem to be Solved by the Invention

In order to solve the above-described problems, according to an aspect of the invention, there is provided an intraocular implant including: a platform portion to which a disk-shaped lens having a lens function of an eye lens of an eye is separably attached; and a support portion which is formed in a leg shape including a first portion extending from the platform portion to the lateral side of the eye and coming into contact with a ciliary sulcus and a second portion divided from a side surface of the first portion and extending toward a ciliary body, supports the platform portion to a rear section inside the eye, and converts the expansion and the contraction of the ciliary body into a front-rear movement of the platform portion inside the eye, wherein the platform portion includes a through-hole portion which causes a beam passing through the lens to pass through the platform portion, and an attachment portion which attaches the lens to the platform portion so that the lens and the through-hole portion overlap each other in a visual axis direction. Accordingly, it is possible to realize an embodiment in which the intraocular implant of the invention is transplanted into the eye and only the lens attached to the implant is replaced after that. Thus, it is possible to more easily replace the intraocular lens compared to the related art.

Further, the attachment portion may separably attach the lens to the platform portion from the front side inside the eye while the platform portion is supported to a rear section inside the eye. Accordingly, since the lens may be replaced from the front side inside the eye while the intraocular implant is transplanted into the eye, it is possible to more easily replace the intraocular lens.

Further, the platform portion may include a hollow portion which is formed inside the platform portion and stores a medicine therein, and a connection hole portion which connects the hollow portion to the outside of the platform portion. Accordingly, the intraocular implant of the invention may also have a function of administering a medicine into the eye. In particular, this configuration is suitable for a case where the medicine needs to be gradually administered for a long period of time.

Further, the support portion may support the platform portion inside the eye while the front end of the support portion comes into contact with the ciliary body and may be formed in a leg shape which converts the expansion and the contraction of the ciliary body into a front-rear movement of the platform portion inside the eye. Accordingly, there is a possibility that the intraocular implant of the invention may adjust the distance to a focusing object by the front-rear movement of the lens in accordance with the patient's focusing action. Thus, there are many possibilities that an intraocular lens having a focus adjustment function may be realized.

Further, according to another aspect of the invention, there is provided an intraocular implant set including: a first intraocular implant which is any one of the above-described intraocular implants and in which the support portion comes into contact with a ciliary sulcus so as to support the platform into the eye; and a second intraocular implant which is any one of the above-described intraocular implants and in which the support portion is fixed to a ciliary flat portion so as to support the platform into the eye. Accordingly, since two intraocular lenses are disposed inside the eye, a visual correction function, a focusing function, and the like are improved, and hence an intraocular lens capable of easily replacing the lens may be realized.

Further, according to still another aspect of the invention, there is provided an intraocular lens including: a disk-shaped lens which has a lens function of an eye lens of an eye; and an intraocular implant which is transplanted into the eye and supports the lens inside the eye, wherein the intraocular implant includes a platform portion to which the lens is separably attached, and a support portion which supports the platform portion to a rear section inside the eye, and wherein the platform portion includes a through-hole portion which causes a beam passing through the lens to pass through the platform portion, and an attachment portion which attaches the lens to the platform portion so that the lens and the through-hole portion overlap each other in a visual axis direction. Accordingly, it is possible to realize an embodiment in which the intraocular implant of the invention is transplanted into the eye and only the lens attached to the implant is replaced after that. Thus, it is possible to more easily replace the intraocular lens compared to the related art.

DETAILED DESCRIPTION OF THE PREFERRED EMBODIMENTS

Figure 1:
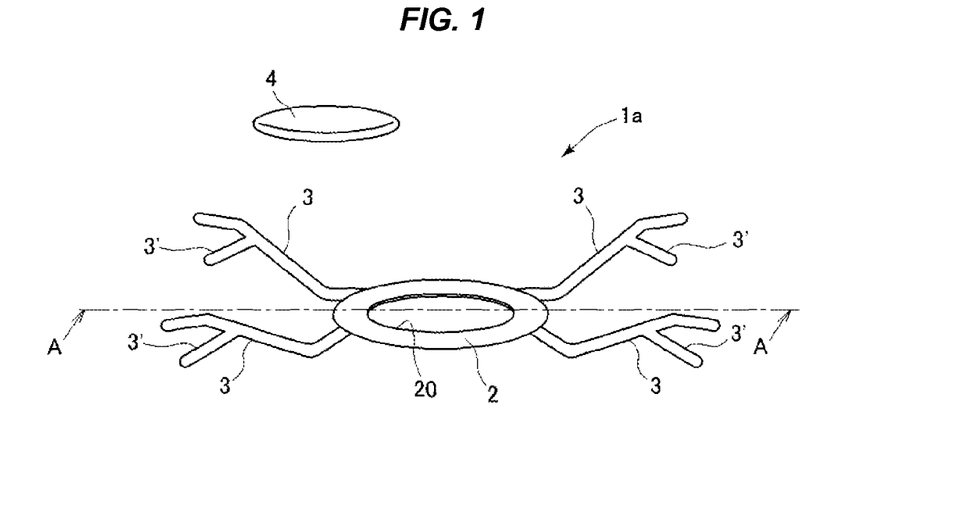
FIG. 1 is a view illustrating an embodiment of an intraocular implant and an intraocular lens of the invention.
Figure 2:
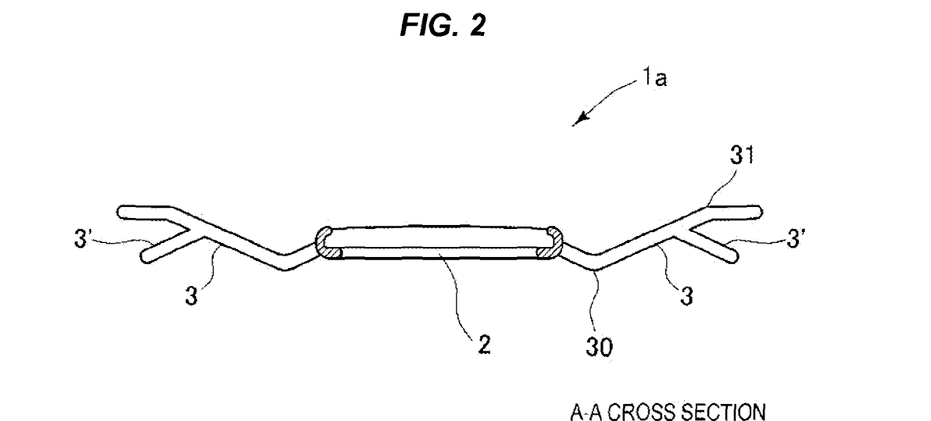
FIG. 2 is a cross-sectional view taken along the line A-A of FIG. 1.
Figure 3:
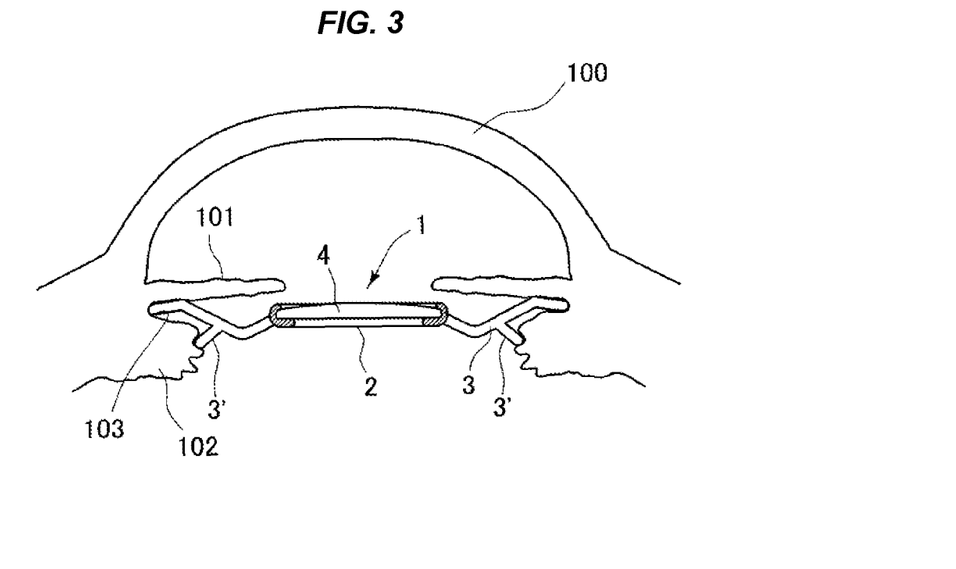
FIG. 3 is a view illustrating an example in the state where the intraocular implant and the intraocular lens of FIG. 1 are attached into an eye.

Hereinafter, an embodiment of the invention will be described with reference to the drawings. First, FIGS. 1 to 3 illustrate an intraocular lens support structure 1 (a support structure and an intraocular implant) of an embodiment of the invention. FIG. 1 is a perspective view of the support structure 1, and FIG. 2 is a cross-sectional view taken along the line A-A. Furthermore, in the description below, the description on the direction such as the front direction, the rear direction, the side direction, and the front surface is made based on the direction (the front direction, the rear direction, the side direction, the front surface, and the like) of a face (or an eye) of a patient in which an intraocular lens is fixed into an eye.

The support structure 1 is a portion used to dispose an intraocular lens 4 (a lens) (in a rear section) inside the eye, and is formed separately from the lens 4. Since the lens 4 is attached to the support structure 1, this configuration becomes the same as that of the existing intraocular lens including a lens used as an eye lens extracted due to the cataract or the like and a portion supporting the lens inside the eye. As will be described later, the support structure 1 and the lens 4 of the invention may be integrally formed with each other inside the eye. Further, according to the invention, it is possible to realize an embodiment in which only the lens 4 is replaced while the support structure 1 is fixed into the eye and which is not present in the related art.

The support structure 1 includes a ring member 2 (a ring) and a leg portion 3. The ring 2 is a member that becomes a platform used to attach the intraocular lens thereto and has a ring shape in which a hole portion 20 is formed at the center thereof. The lens 4 is fixed (attached) into the hole portion 20 (which will be described later in detail).

The leg portion 3 has a shape in which four legs extend from the limbus of the ring 2 toward the lateral side of the eye. Four leg portions 3 are formed at positions where these leg portions are symmetrical to one another in the horizontal and vertical directions when viewed from the direction facing the eye. Each leg portion 3 includes two bent portions 30 and 31. A root portion 32 which is located near the root side in relation to the bent portion 30 in the leg portion 3 is formed so as to be obliquely inclined backward from the limbus of the ring 2.

An intermediate portion 33 which is formed between the bent portion 30 and the bent portion 31 is formed so as to be obliquely inclined forward from the bent portion 30. A front end 34 which is located at the front end side in relation to the bent portion 31 is formed in a direction (substantially) perpendicular to the visual axis of the eye. The front end of the leg portion 3 comes into contact with the ciliary sulcus. As will be described later, such a bent shape is a very suitable shape which transmits the movement of the intraocular tissue as the movement of the lens 4 in the front and rear direction.

Further, the leg portion 3 is divided into two legs at the position between the bent portion 30 and the bent portion 31. A sub-leg portion 3' which is located at one side of the divided portions extends obliquely backward from the divided position. The front end of the sub-leg portion 3' comes into contact with the pleat portion of the ciliary body. The leg portion 3 and the sub-leg portion 3' may be integrally formed with the ring 2 by, for example, a resin material or the like. Alternatively, a structure may be employed in which these leg portions are formed separately from the ring 2 and are coupled (attached) to each other.

The lens 4 has a structure in which the support portion (for example, the haptic portion or the like) of the existing intraocular lens is removed. In a case where the lens 4 is a convex lens, the lens basically has a disk shape, a shape in which the front and rear surfaces thereof are swollen in a convex shape, and a shape in which the lens is thickened as it goes closer to the imaginary center axis. In the case of a concave lens, the lens basically has a disk shape, a shape in which the front and rear surfaces thereof are depressed in a concave shape, and a shape in which the lens is thinned as it goes toward the imaginary center axis.

FIG. 3 illustrates a cross-sectional view of an eye in which the support structure 1 equipped with the lens 4 is transplanted (attached) into the eye. The lens 4 and the support structure 1 are transplanted to the rear section (the rear side of an iris 101) inside the eye.

The transplantation sequence example is as below. For example, in the state where the eye lens is entirely extracted due to the cataract, an operator incises a part of a cornea 100 and inserts the support structure 1 and the lens 4 to the rear section therefrom. At that time, for example, the support structure 1 and the lens 4 are inserted into the eye while being rolled in a cartridge by using the elasticity (bendability) of the support structure 1 and the lens 4, the front end of the cartridge is pressed to the rear section through the cornea 100, and then the support structure 1 and the lens 4 are discharged thereto.

In a case where the support structure 1 is fixed to the rear section, the front end of the leg portion 3 is inserted into a ciliary sulcus 103, and the front end of the sub-leg portion 3' is fixed while coming into contact with a ciliary pleat portion 102. Furthermore, the contact position of the front end of the leg portion 3 may not be essentially the deepest portion of the ciliary sulcus 103 and may be at least a part inside the ciliary sulcus 103. The length (the size) of the leg portion 3 may be designed such that the leg portion 3 is slightly bent while the front end of the leg portion 3 is inserted into the ciliary sulcus 103. Regarding the contact of the sub-leg portion 3' at the ciliary pleat portion 102, the front end of the sub-leg portion 3' may be press-inserted into the surface of the ciliary pleat portion 102.

Any portion of the support structure 1 may not be sutured into the eye. By the above-described fixing method, the support structure 1 is reliably fixed to the rear section. The operator may fix the lens 4 to the support structure 1 inside the eye. Alternatively, the lens 4 may be fixed to the support structure 1 before the support structure 1 is fixed into the eye. When the lens 4 is fixed to the support structure 1, the lens 4 is also reliably fixed into the eye.

In the invention, only the lens 4 may be replaced while the support structure 1 is fixed into the eye after the lens 4 and the support structure 1 are attached into the eye as described above. In that case, as described above, for example, the cornea is incised, a new lens is inserted therefrom by, for example, the above-described cartridge instrument or the like, the lens 4 attached at that time point is separated from the support structure 1, and the new lens 4 is attached to the support structure 1.

The support structure 1 of the invention has a function capable of moving the position of the lens 4 in the front and rear direction by the action (the reflex action) in which the patient's eye tries to focus on an object. The function will be described by referring to FIG. 4.

Figure 4:
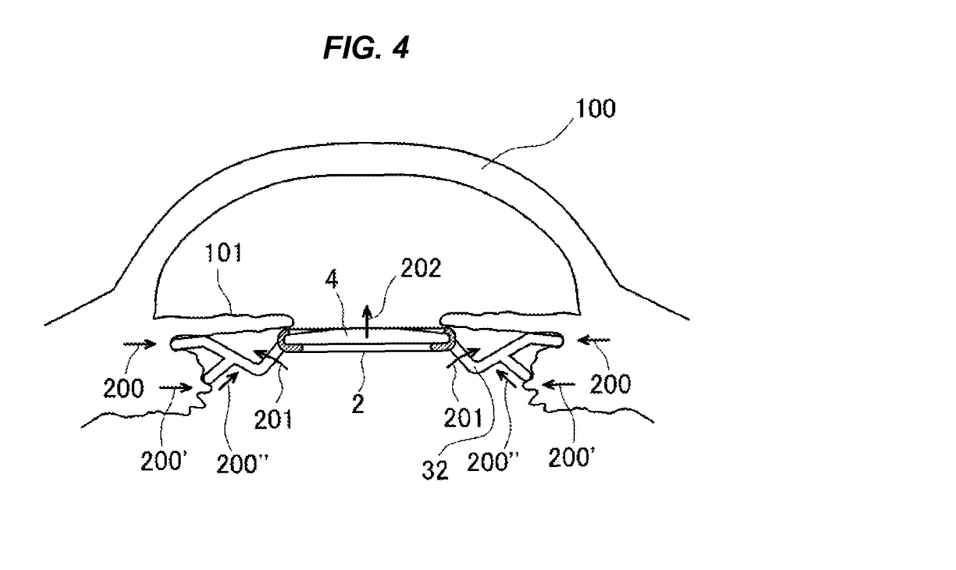
FIG. 4 is a view illustrating an example in the state where the intraocular lens moves due to the action of an intraocular tissue.

According to the medical knowledge, a force is exerted in the direction indicated by the arrow 200 or 200' illustrated in FIG. 4 (the ciliary body expands) in a case where a human's eye tries to focus on an object. This force twists the support structure 1 as illustrated in FIG. 4 by exerting the force of the arrow 200" or the like in the leg portion 3 of the support structure 1. That is, the bent portion 31 is pressed in the direction of the lens 2, and hence the root portion 32 of the leg portion 3 changes to the posture where the root portion becomes more perpendicular to the ring 2.

Accordingly, the posture of the root portion 32 changes in the direction of the arrow 201, and hence the ring 2 and the lens 4 are pressed forward inside the eye. When the force of the arrow 201 disappears (the ciliary body contracts), the ring 2 and the lens 4 return to the original positions. In this way, when the lens 4 moves in the front and rear direction, the distance with respect to a visual object formed as an image on a retina by the lens 4 also changes. Accordingly, the patient with the support structure 1 and the intraocular lens 4 may focus on not only an object in a single distance, but also an object within any distance range from himself or herself.

Figure 5:
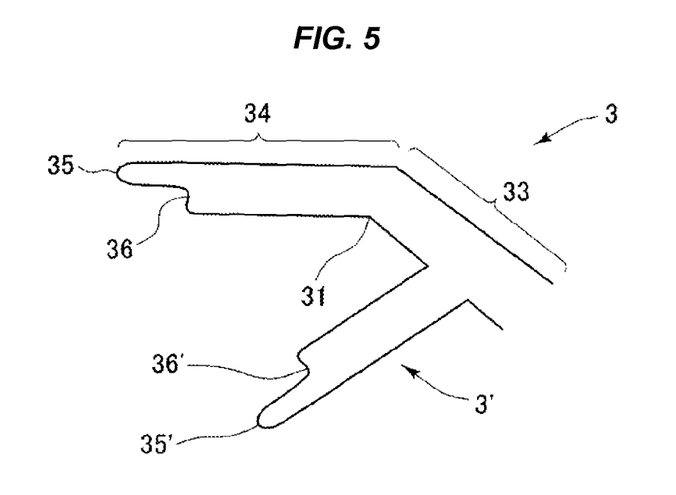
FIG. 5 is a view illustrating an example of a front end of a support portion.
Figure 6:
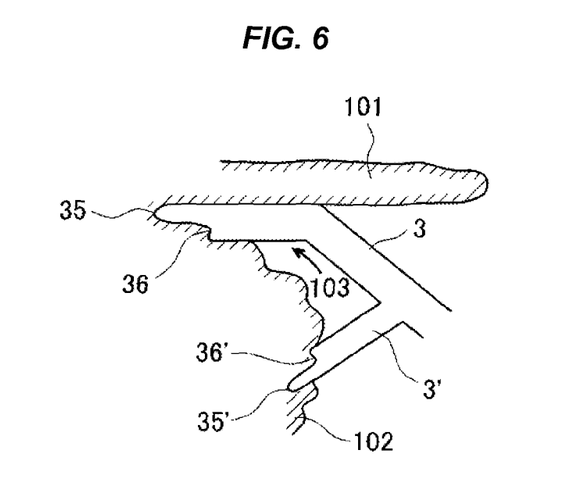
FIG. 6 is a view illustrating an example in which the front end of FIG. 5 is disposed inside an eye.

In the invention, the front end shapes of the leg portion 3 and the sub-leg portion 3' may be improved further. Specifically, as illustrated in FIG. 5, the front ends of the leg portion 3 and the sub-leg portion 3' may be provided with concave portions 36 and 36'. Accordingly, as illustrated in FIG. 6, the front ends 35 and 35' of the leg portion 3 and the sub-leg portion 3' respectively enter the ciliary sulcus 103 and the ciliary body (the pleat portion) 102, the tissue of the ciliary sulcus 103 enters the concave portion 36, and the tissue of the ciliary pleat portion 102 enters the concave portion 36'. Thus, it is desirable to form the concave portions 36 and 36' in that the support structure 1 is more reliably fixed into the eye.

In particular, according to the knowledge found by the present inventor, there is a tendency that the ciliary body 102 is enlarged and the ciliary sulcus 103 is narrowed after the eye lens is extracted. Since the intraocular tissue strongly enters the concave portions 36 and 36' due to such a deformation, the effect of fixing the position of the support structure 1 may be further improved. It is desirable that the concave portion 36 be formed at a position opposite to the iris (a position facing the ciliary body) when the leg portion 3 is fixed into the eye and be formed at a position close to the front end so that the concave portion comes into contact with the enlarged (deformed) ciliary sulcus. Furthermore, the invention is not limited to a case where only concave portions 36 and 36' are formed. For example, an uneven shape (for example, a plurality of concave and convex portions) may be formed in which the intraocular tissue enters (or the uneven shape is fitted to the uneven shape of the intraocular tissue).

Figure 7:
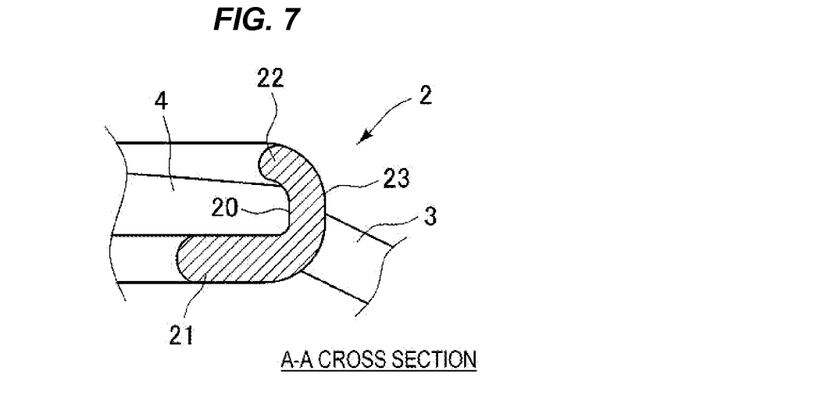
FIG. 7 is a view illustrating a first example of a ring shape.
Figure 8:
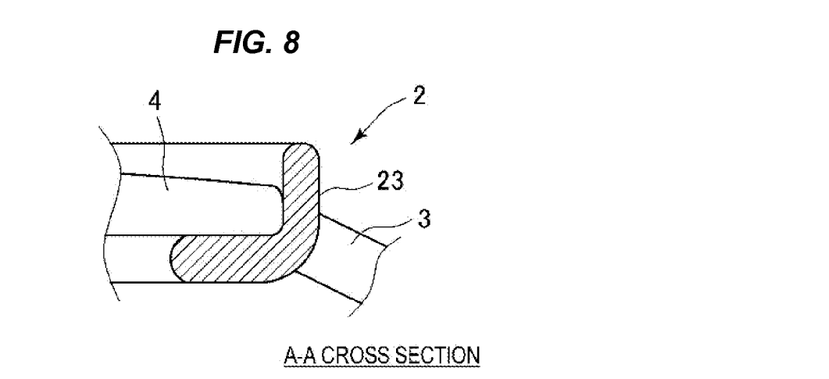
FIG. 8 is a view illustrating a second example of a ring shape.

Next, the shape of the ring 2 will be described in detail. FIGS. 7 and 8 illustrate two examples of the shape of the ring 2. As illustrated in FIG. 2, the ring 2 is formed in a ring shape which has a through-hole portion 20 formed at the center portion thereof. The through-hole portion 20 is formed so that the beam passing through the lens 4 (the beam passing through the cornea, the lens, and the retina) is not disturbed by the existence of the ring 2 and the ring portion around the through-hole portion 20 supports the lens 4.

In the example of FIG. 7, the ring portion around the ring 2 supports the lens 4 so as to surround the limbus thereof. Specifically, as illustrated in FIG. 7, the ring portion around the ring 2 is formed so as to have a substantially U-shaped cross-section, and includes a rear portion 21, a front portion 22, and a side portion 23. The rear portion 21 covers the limbus of the ring 2 from the rear side thereof. The front portion 22 covers the limbus of the ring 2 from the front side thereof. The side portion 23 covers the limbus of the ring 2 from the lateral side (the outside in the radial direction).

The ring 2 of FIG. 7 may be formed of, for example, an elastic material such as rubber or resin. Then, in a case where the lens 2 is attached, the front portion 22 is slightly bent (elastically deformed) and the lens 2 is pressed from the front side. For this reason, in the example of FIG. 7, the width of the front portion 22 in the radial direction is set to be shorter than the width of the rear portion 21 in the radial direction, and hence the lens 2 may be easily pressed from the front side. Furthermore, the front portion 22 may be continuously formed in the entire circumference or may be intermittently formed (as a plurality of portions) at an interval in the circumferential direction.

In the example of FIG. 8, the front portion 22 is not formed compared with FIG. 7. Then, the side portion 24 is also formed in a substantially linear shape. In this shape, the lens 4 is slid on the inner wall of the side portion 24 and is inserted into the ring 2. Of course, the sizes of the ring 2 and the lens 4 may be designed so that the press-inserting operation is performed by a relatively small force in an eye surgery. The lens 4 is fixed into the ring 2 due to the friction between the limbus of the lens 4 and the inner wall of the side portion 24.

Figure 9:
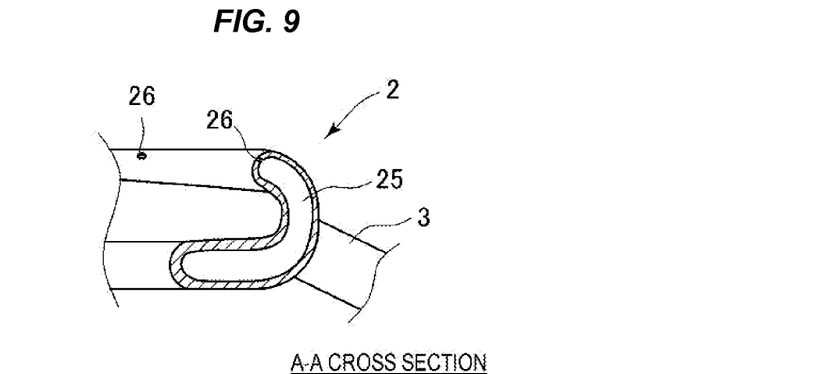
FIG. 9 is a view illustrating an example of a structure used to administer a medicine.

In the invention, the ring 2 may have a function of administering (supplying) a medicine into the eye. An example of a structure for such a function is illustrated in FIG. 9. In this example, a hollow portion 25 is formed inside the ring 2 in the circumferential direction and a connection hole portion 26 is formed so as to connect the hollow portion 25 to the outside of the ring 2. The hollow portion 25 may be formed in the entire circumference. The connection hole portion 26 may be formed as a plurality of portions in the circumferential direction at an interval or may be formed as only a single portion.

The hollow portion 25 is formed so as to store the medicine. The medicine may be injected from the connection hole portion 26 into the hollow portion 25 through, for example, an injection needle having a front end inserted into the eye while the support structure is transplanted into the eye. Accordingly, since the medicine stored in the hollow portion 25 gradually permeates the eye through the connection hole portion 26, this configuration is suitable for a case where the medicine needs to be gradually administered into the eye for a long period of time. The connection hole portion 26 may be formed at the front position inside the eye in relation to the lens 2 while the lens 4 is attached into the ring 2. Accordingly, it is possible to easily inject the medicine from the connection hole portion 26 to the hollow portion 25 through the injection needle or the like while the ring 2 and the lens 4 are attached into the eye. A member such as a sponge storing the medicine by permeation may be disposed inside the hollow portion 25.

In the support structure of the invention, the shape of the leg portion is not limited to the shape of FIG. 1. Different examples of the shape of the leg portion are illustrated in FIGS. 10 to 13. The example of FIG. 10 corresponds to a case where the leg portion has a so-called haptic shape (tactile shape). That is, a pair of haptic portions 5 extends laterally in a circular-arc shape (a loop shape) from two positions (the symmetrical positions with respect to the center axis) of the limbus of the ring 2. The haptic portion 5 may be integrally formed (molded) with the ring 2. Alternatively, the haptic portions 5 may be formed separately from the ring 2 and may be coupled (attached) to each other.

Figure 11:
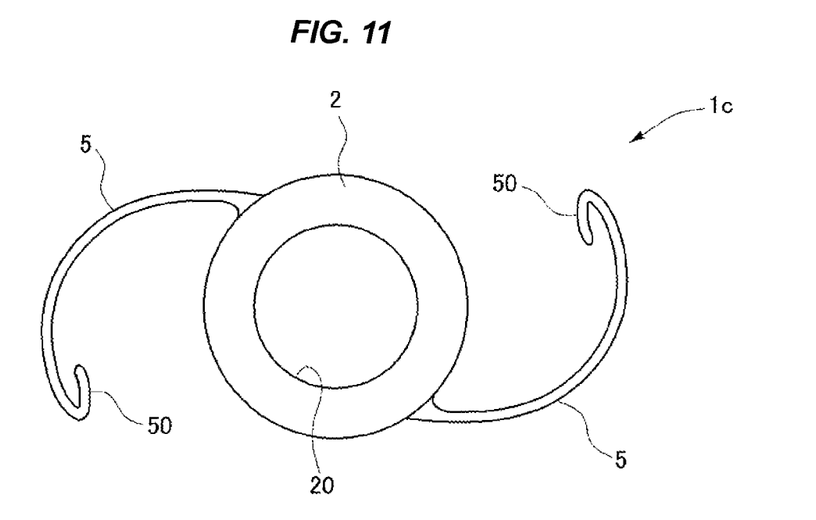
FIG. 11 is a view illustrating an example of an intraocular implant with two haptic portions and folding-back portions.

In the example of FIG. 11, a folding-back portion 50 which is folded back and extends in the opposite direction is formed at the front end of the haptic portion 5. The shape of the folding-back part in the folding-back portion 50 may be a shape in which the folding-back portion is folded back with a corner or is folded back in a curve shape without a corner.

Figure 10:
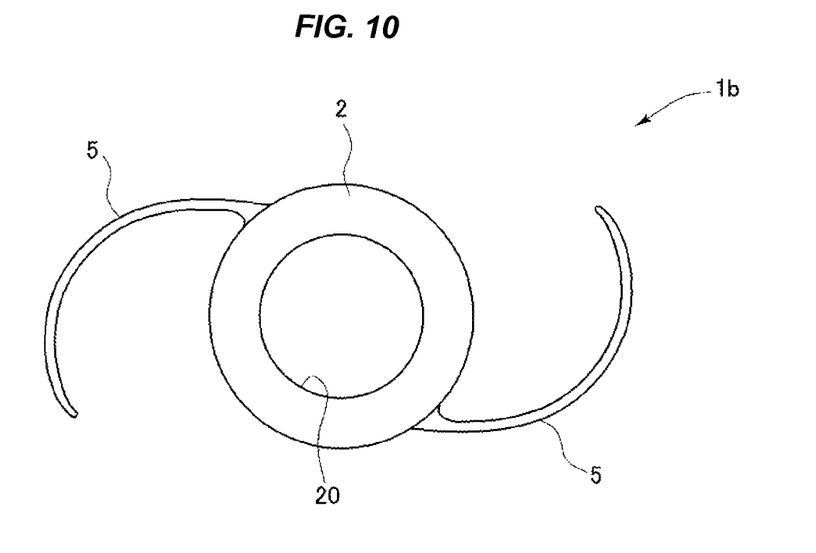
FIG. 10 is a view illustrating an example of an intraocular implant with two haptic portions.
Figure 12:
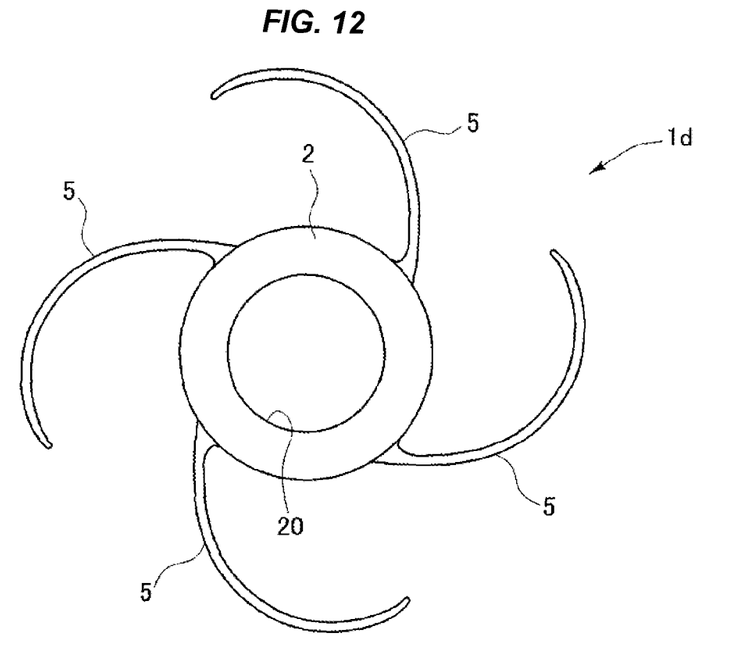
FIG. 12 is a view illustrating an example of an intraocular implant with four haptic portions.

The example of FIG. 12 is an example in which four haptic portions 5 are formed as in the case of FIG. 10. The haptic portions 5 may be formed at the same interval in the circumferential direction. The example of FIG. 13 is an example in which the folding-back portion 50 illustrated in FIG. 11 is formed in each of the front ends of four haptic portions 5 of FIG. 12.

Figure 13:
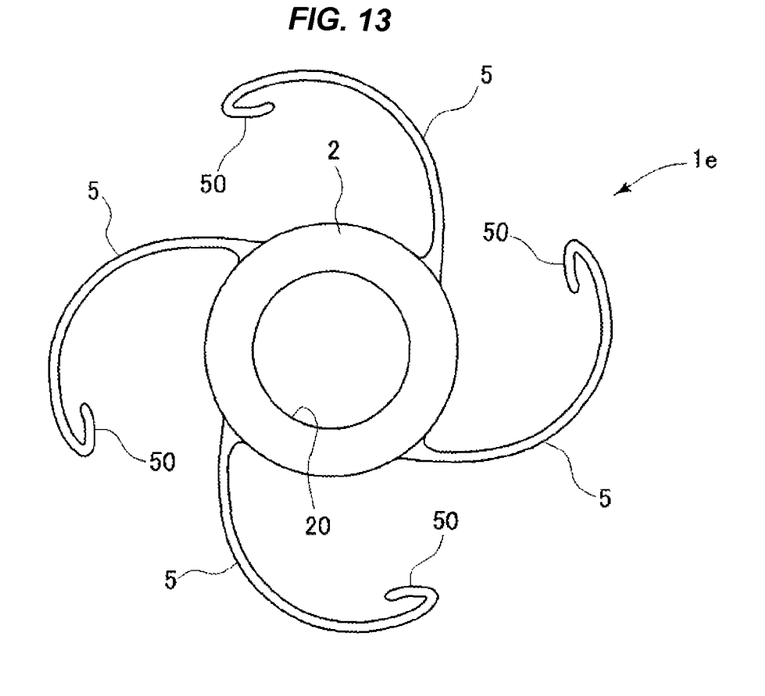
FIG. 13 is a view illustrating an example of an intraocular implant with four haptic portions and folding-back portions.

As such an example, the haptic portion 5 may have elasticity and the folding-back portion 50 and the other portion are separated from each other as illustrated in FIGS. 11 and 13, for example, in the natural state (that is, the state where no force is exerted from the outside). In this case, when the folding-back portion 50 is folded back (that is, the folding-back portion 50 is deformed so as to overlap the other haptic portion 5 in a linear shape, an elastic restoration force is exerted so that the folding-back portion 50 is separated from the other portion as illustrated in FIGS. 11 and 13. Alternatively, the bent portion of the front end of the haptic portion 5 may not have the above-described sufficient elasticity and may be maintained in the shape illustrated in FIGS. 11 and 13.

Regarding the folding-back state of the folding-back portion 50, the folding-back portion may be folded back with a corner or may be folded back in a curve shape without a corner as described above. However, the angle of the folding-back portion may be set so that the folding-back portion is not opened too wide. For example, the angle of the folding-back portion may be set so that the folding-back portion 50 and the other haptic portion 5 may be inserted into the sclera tunnel as will be described below from the folding-back portion as the leading portion.

For example, scale marks may be marked on the folding-back portion 50 in the longitudinal direction at an interval by, for example, printing. A plurality of the scale marks may be formed, and the interval of the scale marks may be the same interval, for example, 0.5 mm. Only one scale mark may be formed.

Since the support portion of the intraocular lens 1 is formed of the same material as that of the existing intraocular lens, when the operator bends the folding-back portion 50 at an appropriate position by using an appropriate medical instrument, the folding-back portion is separated in a comparatively easy manner. Accordingly, when the operator bends the folding-back portion 50 at a position of an appropriate length based on the scale mark, the length of the folding-back portion 50 may be simply adjusted. Thus, the length of the folding-back portion 50 may be set to an appropriate length in response to the length of the sclera tunnel to be described later.

Figure 14:
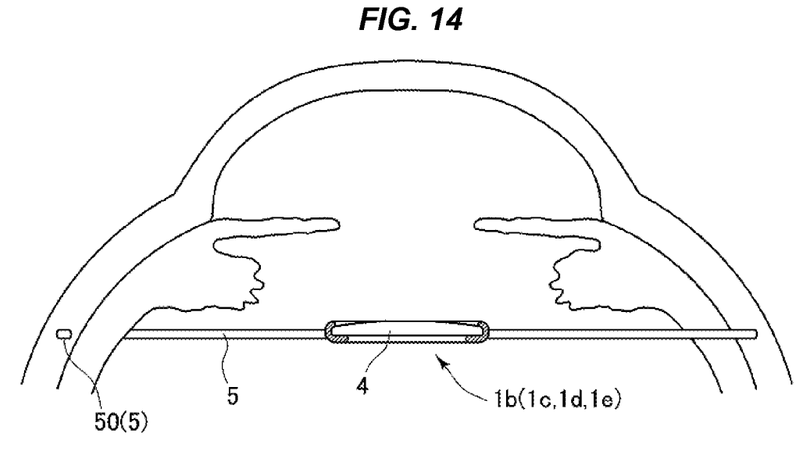
FIG. 14 is a view illustrating an example of the state where the intraocular implants and the intraocular lenses of FIGS. 10 to 13 are attached into an eye.

An example in which the support structure of FIGS. 10 to 13 is transplanted into the eye along with the lens 4 is illustrated in FIG. 14. A support structure 1b (1c, 1d, 1e) is fixed to the rear section (the eye rear section) inside the eye from which the cloudy white eye lens is entirely or partially extracted due to, for example, the cataract by a so-called sclera inside fixing method (without suturing). As illustrated in FIG. 14, in the state where the ring 2 (and the lens 4 attached to the ring) is disposed at the position behind the iris, the front ends (including the folding-back portions 50 in the case of the support structures 1c and 1e) of two or four haptic portions 5 extending from the ring 2 are buried inside the sclera through the ciliary flat portion. In the example of FIG. 14, the eye lens is entirely extracted.

An example of a sclera inside fixing procedure is as below. After the periectomy or the like, a sclera-half-layer valve having a thickness of about a half of the sclera is formed at the position (for example, two (or four) positions symmetrical to each other with respect to the visual axis at the position adjacent to the limbus in the sclera surface) adjacent to the limbus of the cornea in the sclera. Then, a sclera incision is formed in a direction from one position of the lower layer of the sclera-half-layer valve in the sclera toward, for example, the center of the eye ball (for example, toward the ciliary flat portion). Further, a sclera tunnel is formed in a direction substantially parallel to the limbus, that is, the circumferential direction involving with the visual axis by using a position serving as an entrance and substantially located at, for example, the half depth of the sclera thickness from the sclera surface in the side wall of the portion where the sclera-half-layer valve is perforated. The sclera tunnel may be formed so as to perforate the sclera surface as an exit while having an appropriate length (for example, 2 mm to 3 mm).

Then, the support structure 1b (or 1c, 1d, 1e) is rolled in a bar shape, and is inserted from, for example, the incision formed in the cornea into the eye by a predetermined injector. In the state where the sclera-half-layer valve is opened, the front end (including the folding-back portion 50 in the case of the support structure 1c) of the haptic portion 5 inserted into the eye is extracted from the ciliary flat portion through the sclera incision by an appropriate instrument, and is exposed to the outside of the eye from the lower portion of the sclera-half-layer valve. At that time, the entire folding-back portion 50 is exposed to the eye.

Then, the bent portion of the folding-back portion 50 exposed to the outside of the eye is extracted from the exit of the sclera surface of the sclera tunnel formed as described above, and the front end (including the entire folding-back portion 50 in the case of the support structure 1c) of the haptic portion 5 is inserted into the sclera tunnel.

In order to enable the insertion, it is desirable to set the folding-back angle of the folding-back portion 50 as an angle in which the folding-back portion and a part of the haptic portion 5 may be inserted into the sclera tunnel. In the case of the support structure 1c, it is desirable to set the length of the folding-back portion 50 as a length in which the entire folding-back portion and a part of the haptic portion 5 are accommodated in the tunnel-shaped hole portion formed inside the sclera. It is desirable to set the length of the folding-back portion 50 as an appropriate length set by the operator in advance. When the above-described procedure ends, two (four) sclera-half-layer valves are closed. At that time, for example, a fiblin glue is applied to (the rear surface) of the sclera-half-layer valve or the facing surface thereof so that the sclera-half-layer valves are stuck to the sclera. The above-described procedure is an example of a main procedure of the method of fixing the intraocular lens into the sclera.

The method of fixing the support structure 1b, 1c, 1d, or 1e into the sclera may be a method that does not form the sclera-half-layer valve. In this method, the sclera-half-layer valve is not performed, and a sclerotomy is performed from the surface of the sclera toward the rear side. Then, the sclera tunnel is formed from the position of about a half of the thickness of the sclera in the sclerotomy in a direction substantially parallel to the limbus, that is, the circumferential direction involving with the visual axis so as to penetrate the sclera surface as an exit by an appropriate length (for example, 2 to 3 mm).

Then, as described above, the haptic portion 5 (including the folding-back portion 50 in the case of the support structures 1c and 1e) is inserted into the sclera tunnel. In this case, the sclera incision may be sutured if necessary after the front end is inserted into the sclera tunnel. Furthermore, the method of fixing the support structure into the sclera is not limited to the above-described two methods, and any sclera inside fixing method may be used.

By the above-described sequence, the support portion 5 is inserted into the sclera tunnel. Accordingly, the sclera having sufficient strength strongly tightens and restrains the front end of the haptic portion 5. Thus, even when a force is exerted in a direction in which the haptic portion 5 is extracted, the separation thereof from the sclera is reliably suppressed. Particularly, in the case of the support structure 1c, the front end of the folding-back portion 50 is latched to a certain position inside the sclera even when a force is exerted in a direction in which the haptic portion 5 is extracted, and hence the separation of the haptic portion 5 from the sclera is more reliably suppressed.

Further, in a case where the bent portion of the folding-back portion 50 has sufficient elasticity, the folding-back portion 50 accommodated inside the sclera tunnel presses the inner wall of the sclera tunnel so as to be opened again by its elastic restoration force, and hence the haptic portion 5 is strongly restrained by the sclera. Accordingly, the separation of the haptic portion 5 from the sclera is strongly suppressed. In the example of FIG. 14, the haptic portion 5 is extracted from the ciliary flat portion to the outside of the eye and is fixed to the sclera. However, such a method of fixing the intraocular lens (the support structure) through the ciliary flat portion is a very suitable method which is not present in the related art.

Figure 15:
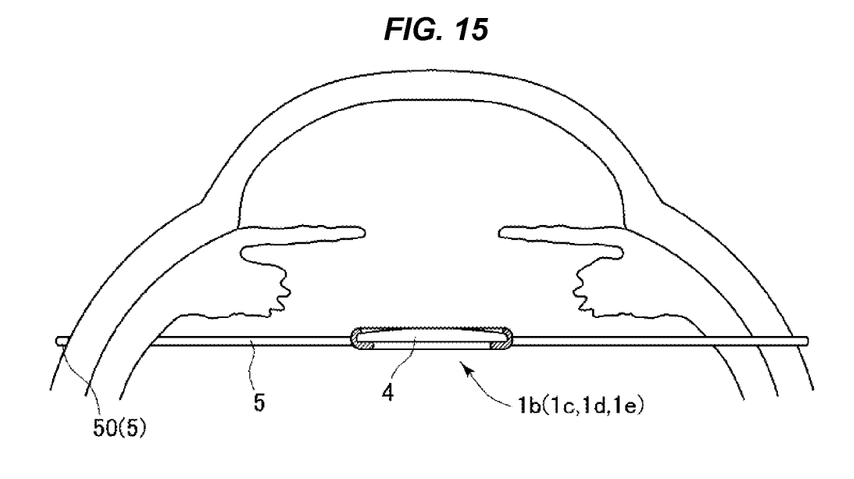
FIG. 15 is a view illustrating another example of the state where the intraocular implants and the intraocular lenses of FIGS. 10 to 13 are attached into an eye.

Alternatively, the support structures 1b, 1c, 1d, and 1e of FIGS. 10 to 13 may be fixed to the outside of the sclera as illustrated in FIG. 15. In this case, the sclera tunnel is not formed according to the above-described procedure, and the haptic portion 5 (including the folding-back portion 50 in the case of the support structures 1c and 1e) is extracted to the outside of the sclera through the ciliary flat portion. In the case of the support structures 1c and 1e, when a force is exerted in a direction in which the haptic portion 5 is extracted, the folding-back portion 50 is latched to the sclera surface so that the separation of the haptic portion 5 is suppressed. Further, in the case of the support structures 1b and 1d, the support structures 1b and 1d may be fixed by suturing the haptic portion extracted to the outside of the sclera to the sclera.

Furthermore, in the above-described method of fixing the support structure, the transplanting operation may be more easily performed when the number of the haptic portions 5 is small as in the case of the support structures 1b and 1c, and the position of the ring may be more stably fixed into the eye when the number of the haptic portions 5 increases as in the case of the support structures 1d and 1e. Particularly, in a case where the support structure is fixed through the ciliary flat portion, it is desirable to provide four haptic portions in that the position of the ring inside the eye may be stabilized.

Figure 16:
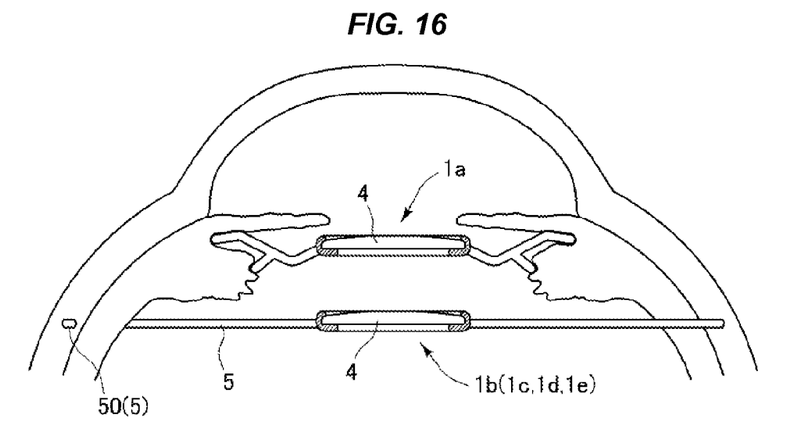
FIG. 16 is a view illustrating an example of the state where the intraocular implant and the intraocular lens of FIG. 1 and the intraocular implants and the intraocular lenses of FIGS. 10 to 13 are attached into an eye.

In the invention, a plurality of the support structures may be transplanted into the eye. FIG. 16 illustrates an example in which the support structure 1a of FIG. 1 and the support structure 1b (1c, 1d, 1e) of FIGS. 10 to 13 are transplanted into the eye. In this example, the support structure 1a at the front side of the eye is supported inside the eye while the front end of the leg portion 3 comes into contact with the deep position of the ciliary sulcus and the front end of the sub-leg portion 3' comes into contact with the ciliary pleat portion. Further, the support structure 1b (or 1c, 1d, 1e) at the rear side of the eye is supported inside the eye while the front end of the haptic portion is fixed into the sclera through the ciliary flat portion. Furthermore, as illustrated in FIG. 17, the support structure 1b (or 1c, 1d, 1e) may be fixed to the outside of the sclera as described above.

Figure 17:
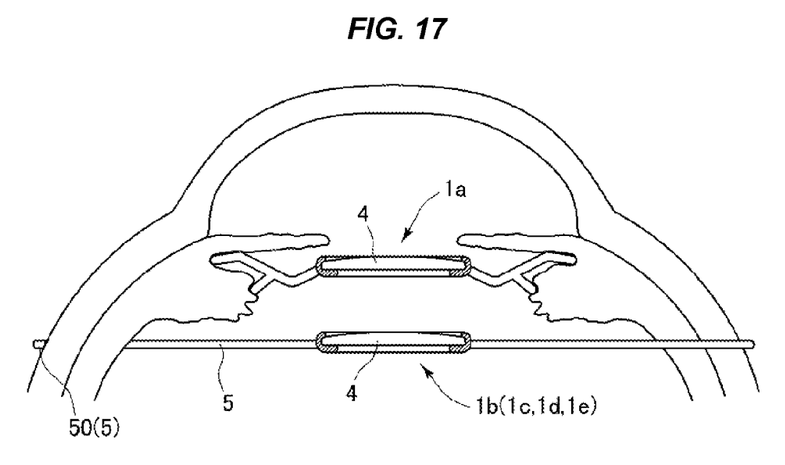
FIG. 17 is a view illustrating another example of the state where the intraocular implant and the intraocular lens of FIG. 1 and the intraocular implants and the intraocular lenses of FIGS. 10 to 13 are attached into an eye.

In the examples of FIGS. 16 and 17, two lenses are disposed inside the eye by attaching the lenses to the support structures. Accordingly, the visual correction effect is improved by two lenses. Further, even in the configurations of FIGS. 16 and 17, the front support structure 1a moves in the front and rear direction by the action of the force in the ciliary body or the like based on the above-described principle. Accordingly, it is possible to relatively largely adjust the distance to the focusing object of the patient's eye by the front-rear movement of one (front) lens of two lenses.

Figure 18:
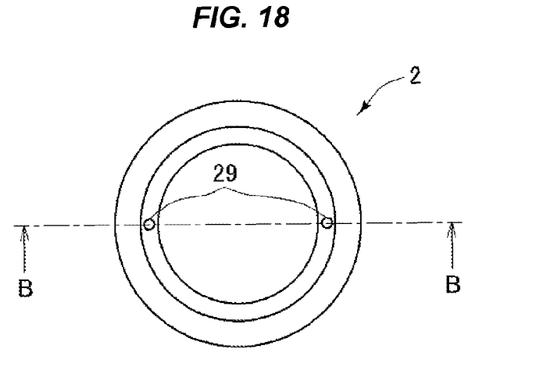
FIG. 18 is a view illustrating a third example of a ring shape.
Figure 19:
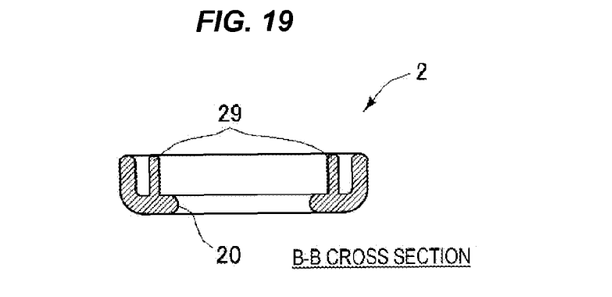
FIG. 19 is a cross-sectional view taken along the line B-B of FIG. 18.
Figure 20:
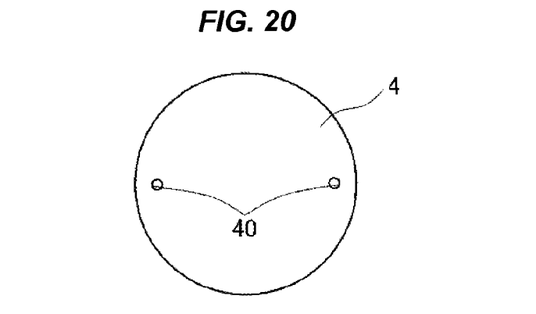
FIG. 20 is a view illustrating an example of a lens.
Figure 21:
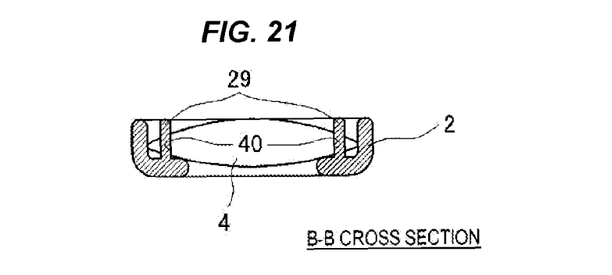
FIG. 21 is a view illustrating an example in which the lens of FIG. 20 is attached to the rings of FIGS. 18 and 19.

In the invention, the embodiment in which the lens 4 is attached to the support structure 1a (1b, 1c, 1d, 1e) is not limited to the description above. FIGS. 18 to 21 illustrate another example of a structure used to attach the lens 4. In this example, the lens 4 is provided with a hole portion, the ring 2 is provided with a protrusion portion, and the lens 2 is attached to the ring 2 by fitting the protrusion portion to the hole portion. In the examples of FIGS. 18, 19, and 21, a protrusion portion 29 is formed at two positions symmetrical to each other with respect to the center axis of the ring 2.

The ring 2 may be any ring of the above-described support structure (or all support structures of the invention). Accordingly, even in the example of FIG. 20, a hole portion 40 is formed at two positions symmetrical to each other with respect to the center axis of the lens 2. When the protrusion portions and the hole portions are fitted to one another as illustrated in FIG. 21, the lens 4 is attached to the ring 2. Furthermore, the protrusion portions 29 are formed so as to protrude toward the front side of the eye when the ring 2 is transplanted into the eye. Accordingly, only the lens 2 may be replaced while the support structure is transplanted into the eye.

The above-described embodiments may be arbitrarily corrected and modified according to the spirit of claims. For example, the number of the leg portions 3 of FIG. 1 is set to four, but the number is not limited to four. That is, six or eight leg portions may be provided as an even number. Further, the number of the haptic portions is set to two or four in the description above, but may be set to an arbitrary number of three, five, six, and the like. The shape of the support portion supporting the lens portion is not limited to the haptic shape or the leg shape. For example, a shape may be employed in which the lens portion may be fixed into the eye by extending the support portion in the radial direction or the circumferential direction involving with the visual axis.

What is claimed is:

1. An intraocular implant comprising:
a platform portion to which a disk-shaped lens having a lens function of an eye lens of an eye is separably attached; and
a support portion which is formed in a leg shape including a first portion extending from the platform portion to the lateral side of the eye and coming into contact with a ciliary sulcus and a second portion divided from a side surface of the first portion and extending obliquely backward from the divided position toward a ciliary body, supports the platform portion to a rear section inside the eye, and converts the expansion and the contraction of the ciliary body into a front-rear movement of the platform portion inside the eye,
wherein the support portion includes a first bent portion, a second bent portion and an intermediate portion formed between the first and second bent portions so as to be obliquely inclined forward from the first bent portion;
wherein the platform portion includes
a through-hole portion which causes a beam passing through the lens to pass through the platform portion, and
an attachment portion which attaches the lens to the platform portion so that the lens and the through-hole portion overlap each other in a visual axis direction.

2. The intraocular implant according to claim 1, wherein the attachment portion separably attaches the lens to the platform portion from the front side inside the eye while the platform portion is supported to a rear section inside the eye.

3. The intraocular implant according to claim 1, wherein the platform portion includes
a hollow portion which is formed inside the platform portion and stores a medicine therein, and
a connection hole portion which connects the hollow portion to the outside of the platform portion.

4. An intraocular implant set comprising:
a first intraocular implant which is the intraocular implant according to claim 1 and in which the support portion comes into contact with a ciliary sulcus and a ciliary body so as to support the platform portion into the eye; and a second intraocular implant which includes a sub-platform portion used to separably attach a disk-shaped lens having a lens function of an eye lens of an eye thereto and a sub-support portion extending from a limbus of the sub-platform portion and having a front end fixed to a ciliary flat portion so that the sub-platform portion is supported to the rear side of the first intraocular implant inside the eye.

5. The intraocular implant according to claim 1, wherein a front end of the first portion is located at a front end side in relation to the second bent portion and is formed in a direction perpendicular to the visual axis of the eye, and a front end of the second portion is formed in a direction not perpendicular to the visual axis of the eye.

6. The intraocular implant according to claim 1, wherein the front end of the first portion and the front end of the second portion are provided with concave portions for respectively receiving tissue of the ciliary sulcus and the ciliary body.

7. An intraocular lens comprising:
a disk-shaped lens which has a lens function of an eye lens of an eye; and
an intraocular implant which is transplanted into the eye and supports the lens inside the eye,
wherein the intraocular implant includes
a platform portion to which the lens is separably attached, and
a support portion which is formed in a leg shape including a first portion extending from the platform portion to the lateral side of the eye and coming into contact with a ciliary sulcus and a second portion divided from a side surface of the first portion and extending obliquely backward from the divided position toward a ciliary body, supports the platform portion to a rear section inside the eye, and converts the expansion and the contraction of the ciliary body into a front-rear movement of the platform portion inside the eye,
wherein the support portion includes a first bent portion, a second bent portion and an intermediate portion formed between the first and second bent portions so as to be obliquely inclined forward from the first bent portion;
wherein the platform portion includes
a through-hole portion which causes a beam passing through the lens to pass through the platform portion, and
an attachment portion which attaches the lens to the platform portion so that the lens and the through-hole portion overlap each other in a visual axis direction.

8. The intraocular implant according to claim 7, wherein a front end of the first portion is located at a front end side in relation to the second bent portion and is formed in a direction perpendicular to the visual axis of the eye, and a front end of the second portion is formed in a direction not perpendicular to the visual axis of the eye.

9. The intraocular implant according to claim 7, wherein the front end of the first portion and the front end of the second portion are provided with concave portions for respectively receiving tissue of the ciliary sulcus and the ciliary body.

* * * * *